US00PP13414P3

(12) United States Plant Patent
van Dijk

(10) Patent No.: US PP13,414 P3
(45) Date of Patent: Dec. 24, 2002

(54) *ANTHURIUM ANDREANUM* PLANT NAMED 'ANTNEROM'

(75) Inventor: Jan van Dijk, De Ruyterweg (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 09/854,669

(22) Filed: May 15, 2001

(65) Prior Publication Data

US 2002/0174474 P1 Nov. 21, 2002

(51) Int. Cl.[7] ..... A01H 5/00
(52) U.S. Cl. ..... Plt./365
(58) Field of Search ..... Plt./365, 369

(56) References Cited

FOREIGN PATENT DOCUMENTS

EP 8568 12/2001

OTHER PUBLICATIONS

UPOV–ROM GTITM Computer Database 2001/01, Feb. 6, 2001, GTI Jouve Retrieval Software, Citation for 'Antnerom'.*

Published proposed denomination; European Community Plant Breeder's Rights Application No. 99/0739.

Published Plant Breeder's Rights Grant; European Community Plant Breeder's Rights Application No. 99/0739 Grant No. EU 8568.

* cited by examiner

*Primary Examiner*—Bruce R. Campell
*Assistant Examiner*—Annette Para
(74) *Attorney, Agent, or Firm*—Foley & Lardner

(57) ABSTRACT

A new and distinct cultivar of Anthurium plant named 'Antnerom', as described and illustrated, and particular characterized by the combined features of very compact plant growth, early and rich flowers; mini-type pot plant that can grow to a maximum of approximately 40 cm; long and erect peduncle, flowers held well above the foliage; very full plant habit due to rich shoot formation; leaves are dark green, very compact, durable with light green primary veins; red and reasonably durable flowers, remaining red for approximately 8 weeks until they die; large flower size in relation to the leaf size resulting in the excellent ratio of leaf to flower size, 2 week root initiation time, 3 cm plant growth per month.

5 Drawing Sheets

LATIN NAME OF THE GENUS AND SPECIES OF THE CLAIMED PLANT

*Anthurium andreanum L.*

VARIETY DENOMINATION

Antnerom.

BACKGROUND OF THE INVENTION

'Antnerom' is a new and distinct cultivar of Anthurium, botanically known as *Anthurium andreanum L.* The new cultivar is a product of a planned breeding program, and was obtained from a cross made during such a program in Bleiswijk, The Netherlands, in 1994.

The female or seed parent was a red-colored Anthurium pot plant having selection number 93-23-31 (unpatented). The male or pollen parent was a proprietary white-colored flowering Anthurium pot plant having selection number 90-106-04 (unpatented). 'Antnerom' was discovered and selected as a flowering plant within the progeny of the stated cross by Jan van Dijk in June 1996 in a controlled environment in a glasshouse in Bleiswijk. Subsequent asexual reproduction by tissue culture at the same location has demonstrated that the combination of characteristics as herein disclosed for the new cultivar are firmly fixed and are retained through successive generations of asexual reproduction.

BRIEF DESCRIPTION OF THE INVENTION

The following observations, measurements and values describe 60 week old plants grown in Bleiswijk, The Netherlands, under greenhouse conditions which closely approximate those generally used in horticultural practice.

The following traits have been repeatedly observed and in combination distinguish 'Antnerom' as a new and distinct cultivar:

1. the plant grows very compact and flowers early and rich;
2. it is a mini-type pot plant that can grow to a maximum of approximately 40 cm;
3. the penducle is long and erect and therefore the flowers are held well above the foliage;
4. the plant habit is very full due to rich shoot formation;
5. the leaves are dark green, very compact, durable with light green primary veins;
6. the flowers are red and reasonably durable, they remain red for approximately 8 weeks until they die;
7. the flower size is large in relation to the leaf size and therefore the ratio of leaf to flower size is excellent.
8. it takes two weeks for the plant to initiate roots; and
9. the plant grows approximately 3 cm per month.

BRIEF DESCRIPTION OF THE DRAWINGS

The accompanying photographs, taken in Bleiswijk, The Netherlands, show typical 'Antnerom' specimens. Color references are made to The Royal Horticultural Society (R.H.S.) Colour Chart, except where general color terms of ordinary significance are used. The color references are approximate, as color depends to a degree on horticultural practices such as light level and degree of fertilization, among others. The color values were determined between 11:00 a.m. and 3:00 p.m. on Feb. 2, 2001, under 5000 lux natural light in a glasshouse in Bleiswijk. The phenotype may vary significantly when grown under different conditions of temperature, light or other determining factors, without a change in genotype of the plant.

The first drawing sheet is a side view of 'Antnerom' showing the flowers held well above the leaf canopy.

The second drawing sheet is a close-up of a 'Antnerom' flower showing the spathe and spadix with pollen.

The third drawing sheet is a close-up of 'Antnerom' flowers at three different development stages. From young on the left to old on the right. The youngest flower has an unripe spadix (pistils and pollen are not visible yet). The flower in the middle has a ripe spadix with a large amount of pollen. The spathe of the old flower on the right becomes brown-red. Between the left and the right flowers is a difference in age of approximately 8 to 10 weeks.

The fourth drawing sheet is a close-up of the top a young (left) and old leaf blade (right) showing the difference between the vein color of young and old leaf blades. It also shows that the young leaf blades are more shiny then the old leaf blades.

The fifth drawing sheet shows 'Antnerom' plants as grown in a glasshouse in Bleiswijk, The Netherlands.

DETAILED BOTANICAL DESCRIPTION

Propagation: Asexual propagation by means of tissue culture and all propagations that flowered have been true to the original type in plant and flower characteristics.

Plant description: Approximately 55–60 weeks following division, 'Antnerom' will reach a mature size of approximately 35 cm to 40 cm in height and approximately 30 cm to 35 cm in width in a 14 cm pot. However, 'Antnerom' can be easily grown to a smaller size for example 25 cm in height, when it is placed in a 12 cm pot.

Leaves:

*Form*.—The leaf blade is elliptical-cordate with an acuminate tip and a cordate base. The leaf blade angle with the petiole between 120 and 150 degrees. 'Antnerom' makes larger leaf blades as it ages. 'Antnerom' also produces a lot of axillary shoots with small leaf blades. Therefore, a wide range in leaf blade length and width is found on each plant. The minimum leaf blade length is approximately 3 cm and the maximum leaf blade length is approximately 14 cm. The minimum leaf blade width is approximately 1.5 cm and the maximum leaf blade length is approximately 10 cm.

*Texture*.—The leaf blades are shiny, leathery and thick. The mature leaf blades are weakly cupped. The young leaf blades of more shiny then the old leaf blades.

*Veins*.—The mid-vein and primary veins (the veins which radiate out from juncture periole and leaf) protude at the underside of the leaf blade. These veins are brown-red (RHS 178B) in young leaf blades (approximately maximum 4 weeks old) and become green as the leaf blades age. In older leaf blades (approx. more then 4 weeks) the green color of the veins at the upper surface (RHS 146B) and the lower surface (RHS 145A) of the mid-vein and primary veins (approximately 4 to 6) contrast with the more darker green color of the upper surface of the leaf blade.

*Leaf blade-color*.—Young leaf blade (approximately maximum 4 weeks old) upper an surface is yellow-green (RHS 152A). Old leaf blade (approximately more than 4 weeks upper surface is green (RHS 139A) and the lower surface is light green (RHS 137C).

*Lobes*.—A leaf blade has two small lobes extending past the petiole. The distance petiole/leaf juncture to the highest point on the lobes of mature leaf blades. (width 8 cm, length 12 cm) ranges approximately from 0.5 to 1.5 cm.

*Petiole*.—The color of the petiole of an old leaf blade is green (RHS 147B). The color of the petiole of a young leaf blade is brown-red (RHS 178B). The cross section of the petiole is round and the diameter is approximately 2 to 3 mm. The color of the cataphyls surrounding the petioles is brown (RHS 165A–B) with a brown-red base (RHS 181A). The petiole length of the leaf blades is 16 to 20 cm, with a width of 8 cm and a length of 12 cm.

Spathe:

*Buds*.—The spathe is tightly rolled around the spadix and extrudes from the peduncle sheath. After the spathe is fully open the peduncle elongates for a few more centimeters.

*Size*.—The completely developed spathe of a 30 cm tall plant is approximately 7 cm to 8 cm long and approximately 6 cm width.

*Color*.—The spathe color was measured in Bleiswijk, The Netherlands. When the spathe is just fully open the upper surface is red (RHS 53B) and the lower sun also red (RHS 53C). Approximately 7 to 8 weeks after the opening of the spathe discolors to brown-red (RHS 178A). The red color slightly disappears. After approximately another 7 to 8 weeks the complete flower will die off.

*Fragrance*.—The plant has no fragrance.

*Arrangement*.—The spathe angle with the peduncle is between 110 and 130 degrees. The spathe stand on a straight wiry peduncle approximately 6 cm to 10 cm above the foliage. The peduncle cross-section is round and the diameter approximately 3 mm to 4 mm, depending on the age of the plant. The peduncle is erect and it's length on the plant-age. It ranges from approximately 10 to 25 cm.

*Shape*.—The spathe is ovate with a mucronate tip and a rotundate base. A just fully opened spathe is slightly cup-shaped. The edges of the spathe stay upwards.

Flowering time: One small tissue culture plant of approximately 2 cm tall will flower, depending on season, after approximately 15 to 16 months when approximately 2 to 3 blossoms will appear. More blossoms appear some weeks later so that a full flowering and salable plant can have 4 to 10 red flowers. Smaller blossoms may occur on less mature growth.

Reproductive organs:

*Size*.—The spadix measures approximately 4 to 6 cm in height. The length of the spandix is equal to the length of the spathe. The spadix is a little columnar. The width mature spadix that is approximately 6 cm long is approximately 9 mm to 10 mm base and approximately 7 mm to 8 mm at the top. The spadix angle with spathe is approximately 50 to 70 degrees.

*Color*.—The spadix color was measured in Bleiswijk, The Netherlands. At the time the spathe unrolls the spadix is fully unripe. Later the spadix will mature: pistils become visible and pollen occurs. An unripe spadix is pink-red (RHS 50B) and a ripe spadix is pink (RHS 54B). As the spadix matures (from base to tip) it becomes fully pink. When pistils have been pollinated, berries exist on the spadix.

*Stamens*.—Anthers and filaments are not clearly visible on the spadix.

*Pollen*.—A large amount does appear and has a white color (RHS 155D).

*Pistil*.—The same color as described for the spadix. The pistil protrudes from the spandix.

*Berries and seeds*.—No information to date.

Roots: Flesh pink-white roots (RHS 159C to RHS 48A), with smaller hairy laterals. The root-tips are yellow (RHS 22A).

Disease/pest resistance: No known resistance and/or susceptibility to diseases and pests.

I claim:

1. A new and distinct Anthurium plant named 'Antnerom', as herein described and illustrated.

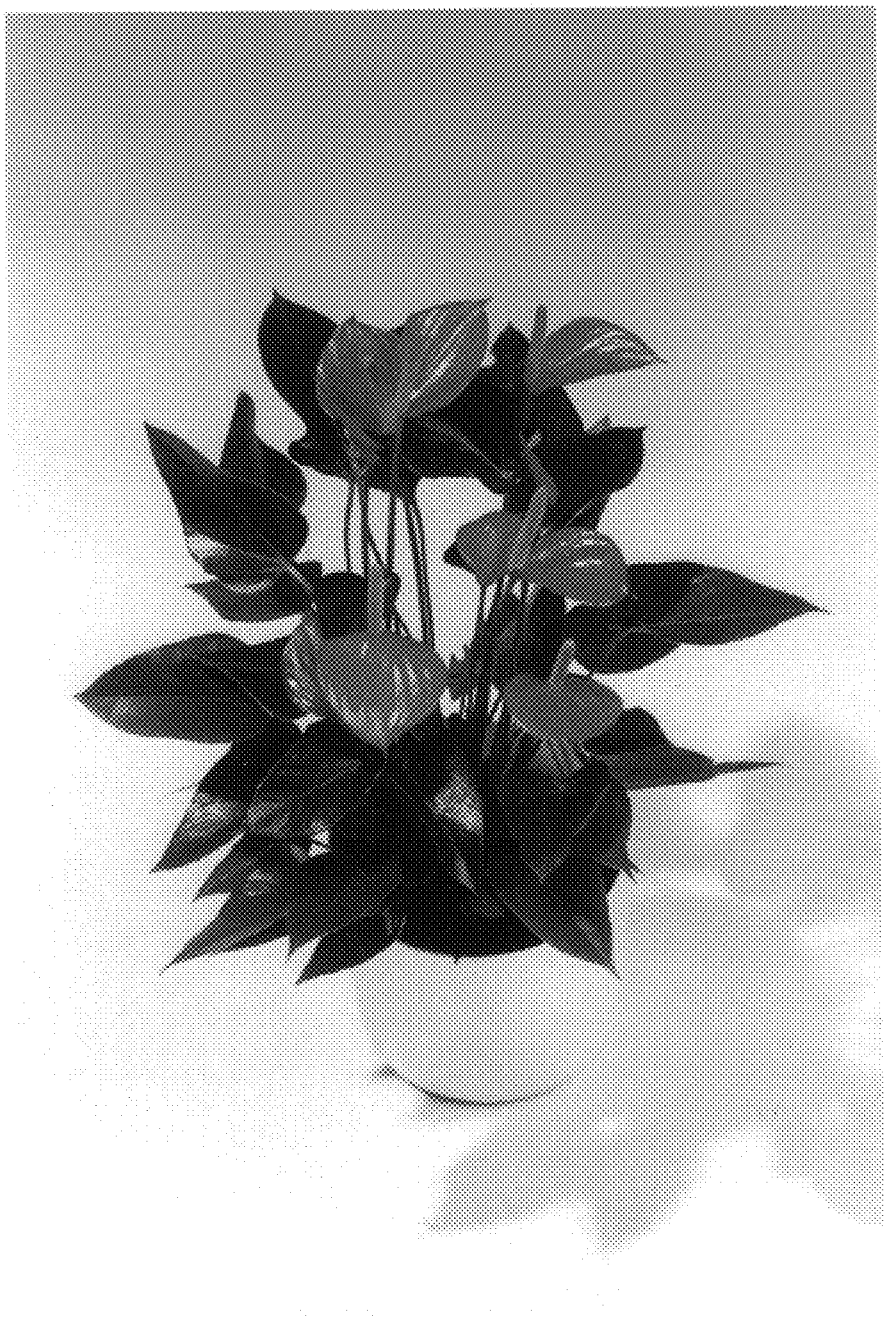

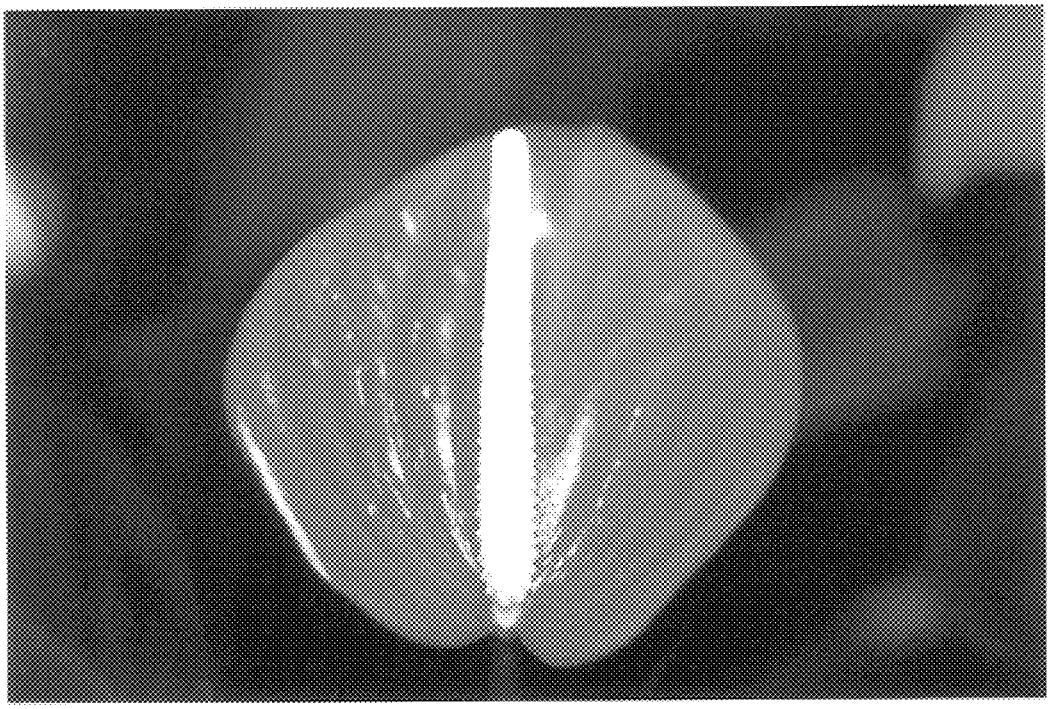

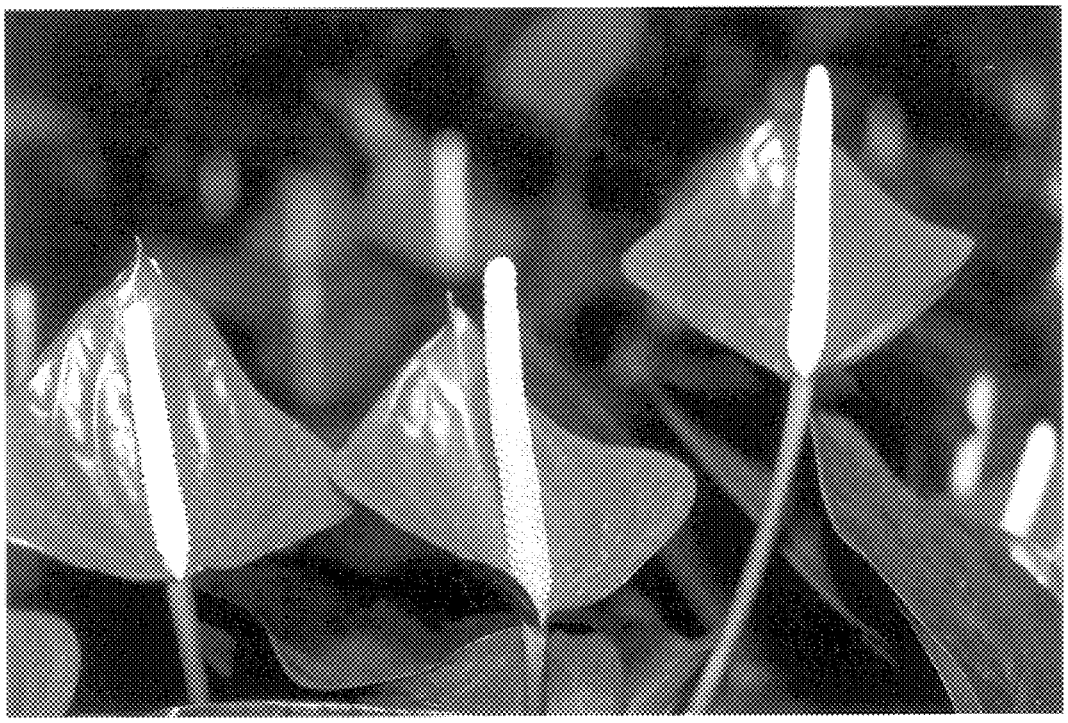

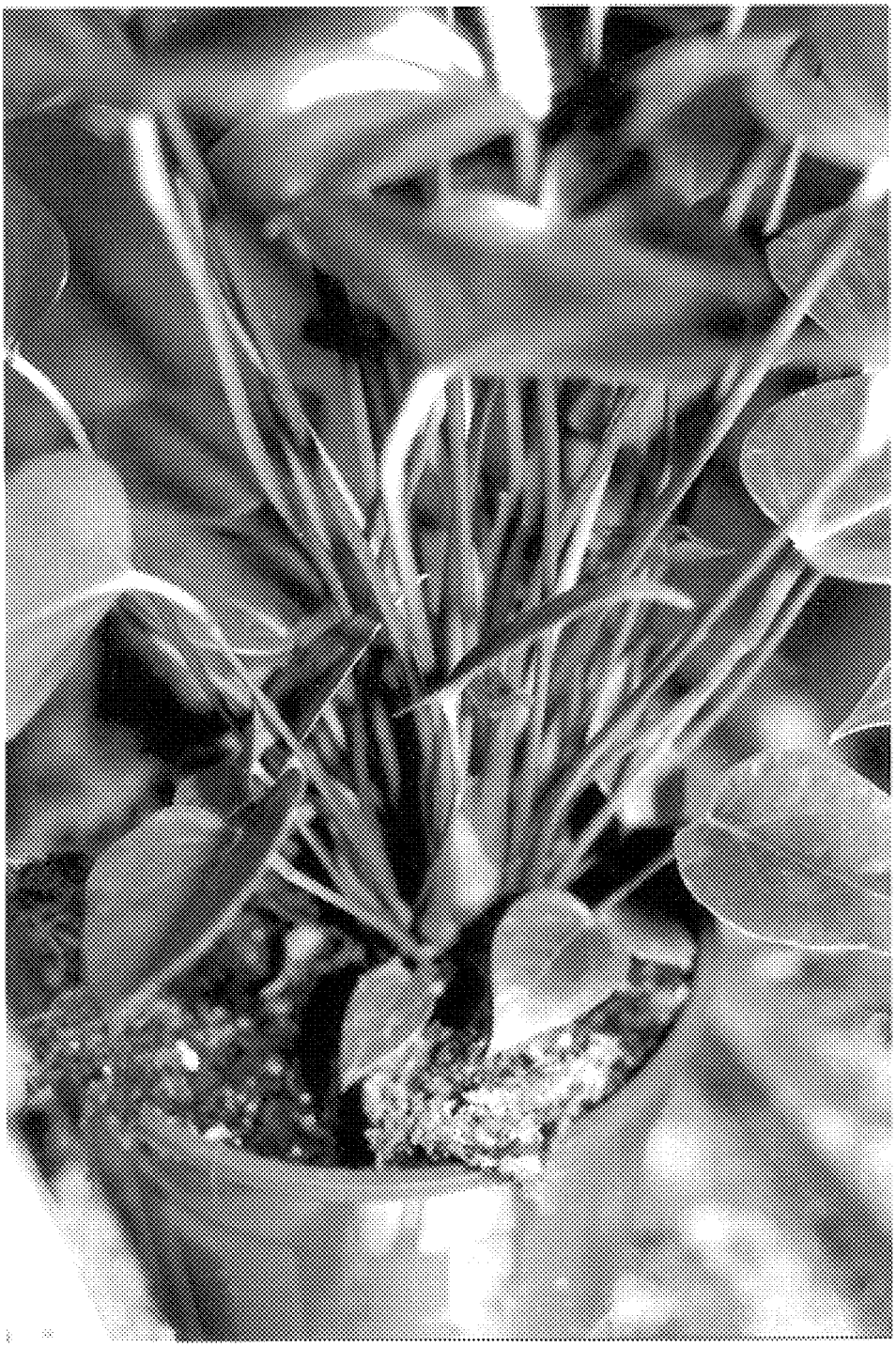

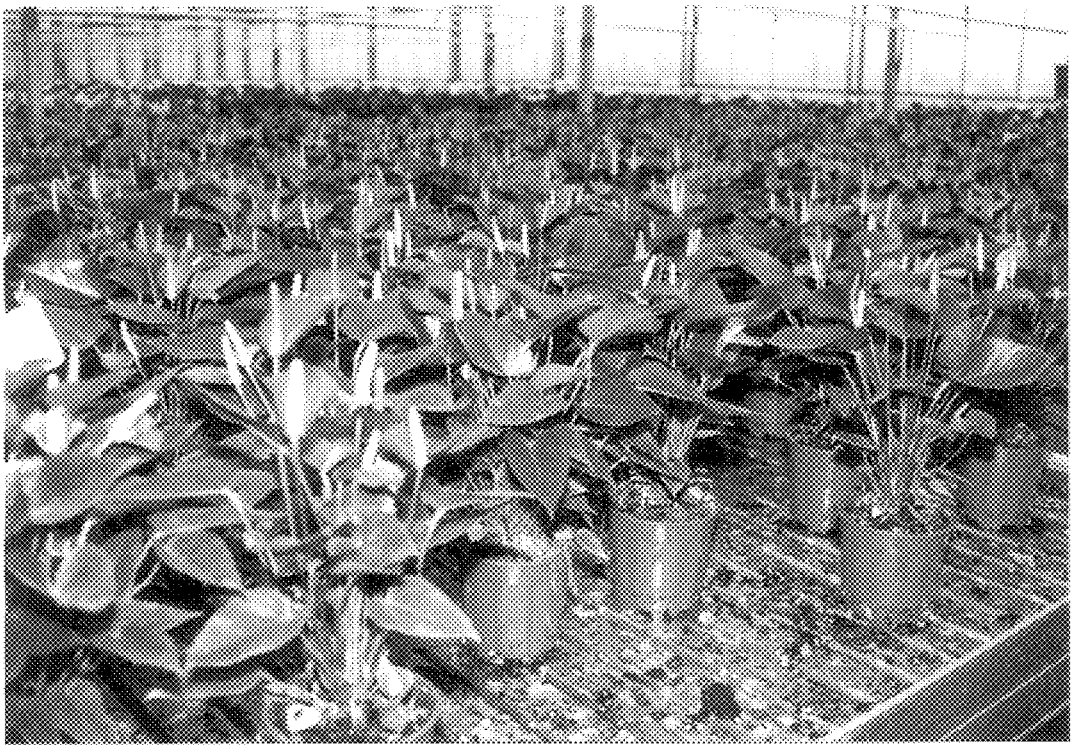

* * * * *